United States Patent
Berndt

(10) Patent No.: US 7,198,806 B2
(45) Date of Patent: Apr. 3, 2007

(54) COMPOSITION AND METHOD FOR TREATMENT AND PREVENTION OF PRURITIS

(76) Inventor: Robert Berndt, 11416 County Line Rd., Des Moines, IA (US) 50320

( * ) Notice: Subject to any disclaimer, the term of this patent is extended or adjusted under 35 U.S.C. 154(b) by 0 days.

(21) Appl. No.: 11/217,765

(22) Filed: Sep. 1, 2005

(65) Prior Publication Data

US 2006/0008545 A1    Jan. 12, 2006

Related U.S. Application Data

(62) Division of application No. 10/611,280, filed on Jun. 30, 2003, now Pat. No. 7,001,622.

(51) Int. Cl.
*A61K 36/00* (2006.01)

(52) U.S. Cl. .................................................. 424/725

(58) Field of Classification Search ................ 424/725
See application file for complete search history.

(56) References Cited

U.S. PATENT DOCUMENTS

| | | | |
|---|---|---|---|
| 5,876,702 A | 3/1999 | Gers-Barlag et al. |
| 5,952,373 A | 9/1999 | Lanzendorfer et al. |
| 6,121,243 A | 9/2000 | Lanzendorfer et al. |
| 6,180,662 B1 | 1/2001 | Lanzendorfer et al. |
| 6,423,747 B1 | 7/2002 | Lanzendorfer et al. |
| 2002/0099095 A1 | 7/2002 | Lanzendorfer et al. |

OTHER PUBLICATIONS

Internet website "Pussytoes" (2002) (2 pages total).*

* cited by examiner

*Primary Examiner*—Christopher Tate
*Assistant Examiner*—S. B. McCormick-Ewoldt
(74) *Attorney, Agent, or Firm*—McKee, Voorhees & Sease, P.L.C.

(57) ABSTRACT

The present invention describes a composition for preventing pruritis or inflammation that includes field pussy-toes plant extract, and methods of using and manufacturing the same. The compositions of this invention have been found to be especially useful in preventing and treating lesions from poison ivy, chicken pox, and cold sores.

4 Claims, No Drawings

COMPOSITION AND METHOD FOR TREATMENT AND PREVENTION OF PRURITIS

GRANT REFERENCE CLAUSE

The present invention has been funded, in part, by DOE Grant No. DE-FG26-02NT41549. The government may have certain rights in this invention.

FIELD OF THE INVENTION

The present invention relates to the antipruitic treatment and prevention of poison ivy and other conditions and disorders characterized by inflammation and/or pruritus using Antennaria Neglecta (field pussy-toes or cat's-foot).

BACKGROUND OF THE INVENTION

Pruritus is a condition involving localized or general itching that is a common and distressing symptom in a variety of diseases. Although usually occurring in the skin, pruritus can also occur in non-cutaneous sites such as mucous membranes. Pruritis is a frequent manifestation of localized skin disorders caused by hypersensitivity reactions such as allergic reactions to insect bites or to environmental allergens, urticaria, dermatoses of fungal and bacterial origins, ectoparasite infections, and hemorrhoids. Pruritis may also be a symptom caused by systemic diseases, including, for example, hypothyroidism, thyrotoxicosis, mucocandiasis in diabetes mellitus, and Hodgkin's disease. (see, for example, Herndon, J. H. Jr., Int. J. Derm. 14, 465–484 (1975); Winkelmann, R. K., Med. Clins. N. Am. 66, 1119–1133 (1982). Many systemic diseases and skin disorders are accompanied by bouts of persistent or recurrent pruritis. The clinical importance of pruritus is irrefutable but effective treatment has been limited by current available treatments.

Current treatments for pruritus include the use of antihistamines and corticosteroids. Both, however, have undesired side effects. Antihistamines may relieve pruritis but can cause drowsiness or dry mouth. Some topical preparations contain chemicals such as corticosteroids but are limited to treating those with a steroid responsive disorder. These messy topical preparations provide relatively short-duration antipruritic activity and must be applied frequently to continue relief from pruritis.

Thus, there is a continuing need for development of new and improved compositions that are inexpensive and effective in treating and preventing inflammation and/or pruritus resulting from a wide variety of causes.

The poison ivy plant and its relatives are ubiquitous throughout the United States. Allergic reactions from these plants will affect millions of Americans every year. Researchers have found that 85% of the population will develop an allergic reaction if exposed to poison ivy. Although allergic contact dermatitis can occur in any setting, many cases are related to exposures in the workplace. Outdoor workers, including surveyors, firefighters, park and highway maintenance workers, utility-line workers, and farm workers are most at risk. When all occupationally related illness in the United States was last estimated, allergic contact dermatitis accounted for 7%, at an annual cost of $250 million in lost productivity, medical care, and disability payments.

Contact with the oil from a poison ivy plant often results in an allergic skin reaction that is manifested by pruritis and bothersome rashes that progress to painful blisters. The oil, urushiol, is found in all parts of the poison ivy plant, including the leaves, stems, roots, and berries. Urushiol is invisible and sticky and may be carried on garden tools or even on pet's fur, where, unless the oil is detected and removed, it maintains its potency on the surface of such objects for years. The rash is spread by touching an area or object contaminated with urushiol and then touching a "clean" area, for example, wiping the forehead with a contaminated hand. In this way, the unaware urushiol-carrier may unknowingly contaminate other areas not initially in direct contact with poison ivy, such as the mouth, genital, or eye areas. Urushiol can penetrate the skin within minutes and the symptoms of pruritis and rashes will not appear for days.

Sensitivity to urushiol can develop at any time and seems to develop over several exposures. Repeated bouts of the allergic contact dermatitis from poison ivy can become more severe. Without treatment, the symptoms of the rash will normally disappear in 14 to 20 days.

For those who are highly sensitive to poison ivy, they may be unable to wait for the symptoms to dissipate. In some cases, contact with poison ivy results in a severe reaction, including swelling of the face and throat. This reaction can impair breathing and warrants immediate treatment at a hospital. For those with less severe reactions not warranting emergency medical treatment, many still cannot handle the itch without some relief.

Thus, the above treatments have not been satisfactory. To prevent poison ivy, the current approach is to learn to recognize the poison ivy plant and simply avoid it. However, as noted previously, certain occupations may be unable to prevent contact with the plants. There is therefore a need in the art for an improved composition and method of treating and preventing pruritis which solves the problems of the aforementioned compositions and methods.

Accordingly, it is a primary objective of the present invention to provide an improved therapeutic method to treat pruritic conditions of the skin or mucous membrane, particularly caused by exposure to poison ivy.

It is a further objective of the present invention to provide an effective therapeutic composition that prevents and treats inflammatory and/or pruritic conditions caused by poison ivy or other diseases and disorders.

It is a still a further objective of the present invention to provide a method for manufacturing compositions to prevent and treat inflammation and/or pruritis.

The method and means of accomplishing each of the above objectives as well as others will become apparent from the detailed description of the invention which follows hereafter.

SUMMARY OF THE INVENTION

One embodiment of the present invention describes a composition for preventing or treating inflammation and/or pruritis comprising a therapeutically effective amount of extract of Antennaria Neglecta (pussy-toes or cat's-foot) plant. The present invention also describes a method for treating inflammation and/or pruritis comprising administering a therapeutically effective amount of (a portion of) pussy-toes plant extract to a patient in need of such treatment using pharmaceutically acceptable vehicles. The present invention also provides a method for manufacturing varying compositions containing pussy-toes extract depending on the preferred modality.

DETAILED DESCRIPTION OF THE PREFERRED EMBODIMENT

As set forth above, the present invention relates to the development of a composition for preventing inflammation/pruritis, a method for treating inflammation/pruritis and manufacturing compositions for treatment or prevention of diseases or disorders related to inflammation/pruritis. While the following disclosure speaks primarily of the invention's use in preventing and treating poison ivy and chicken pox, the invention is broadly intended for use in the prevention and treatment of all types of inflammation/pruritis from various diseases or disorders including, but not limited to, hypersensitivity reactions such as allergic reactions to insect bites or to environmental allergens, urticaria, dermatoses of fungal and bacterial origins, ectoparasite infections, hemorrhoids, hypothyroidism, thyrotoxicosis, mucocandiasis in diabetes mellitus, cold sores, and Hodgkin's disease.

Antennaria Neglecta, more commonly known as field pussy-toes, is one of twenty-five to thirty species of Antennaria worldwide. Field pussy-toes (more simply referred to herein as "pussy-toes") is a member of the sunflower family (Asteraceae).

As used herein, a "therapeutically effective amount" refers to an amount of an active agent sufficient to induce a desired biological result, i.e., prevention or treatment of pruritis or other inflammatory dermatoses. That result may be alleviation of the signs, symptoms, or causes of a disease, or any other desired alteration of a biological system. The amount that is "effective" will vary from subject to subject, and it is not always possible to specify an exact "effective" amount. However, an appropriate "effective" amount in any individual case may be determined by one of ordinary skill in the art using routine experimentation.

Before describing the present invention in detail, it is to be understood that this invention is not limited to carriers, formulation types, treatment regimens, and so forth, as such may vary. It is also to be understood that the terminology used herein is for the purpose of describing particular embodiments only, and is not intended to be limiting. It must be noted that, as used in this specification and the appended claims, the singular forms "a," "an," and "the" include plural referents unless the context clearly dictates otherwise.

Pussy-toes plant extract may be generally used for the prophylaxis and treatment of diseases and disorders that involve inflammation and/or pruritis. In one embodiment of the invention, pussy-toes plant extract is administered to a patient directly. The extract may be removed from the field pussy-toes plant by conventional means, including by pressing, crushing, masticating, or heating portions of the plant. In one embodiment, the leaves of Antennaria Neglecta are masticated by the patient and the juice or extract swallowed. In another embodiment, the leaves or other portions of the plant, such as the flower, stem or roots, are heated in water to form a "tea", the leaves removed from the water, and the resulting aqueous extract administered.

In the alternative, pussy-toes plant extract may be administered in a pharmaceutically acceptable carrier. Any pharmaceutically acceptable carrier may be generally used for this purpose, provided that the carrier does not significantly interfere with the stability or bioavailability of the compounds of this invention.

The compounds of this invention can be administered in any effectively pharmaceutically acceptable form to warm blooded animals, including human and other animal subjects, e.g. in topical, lavage, oral, suppository, parenteral, or infusible dosage forms, as a topical, buccal, sublingual, or nasal spray or in any other manner effective to deliver the agents. The route of administration will preferably be designed to optimize delivery and/or localization of the agents to target cells.

In addition to the active compounds i.e. extract of pussy-toes plant, the pharmaceutical compositions of this invention may contain suitable excipients and auxiliaries which facilitate processing of the active compounds into preparations which can be used pharmaceutically. Oral dosage forms encompass tablets, capsules, and granules. Preparations which can be administered rectally include suppositories. Other dosage forms include suitable solutions for administration parenterally or orally, and compositions which can be administered buccally or sublingually.

The pharmaceutical preparations of the present invention are maruifactured in a manner which is itself well known in the art. For example the pharmaceutical preparations may be made by means of conventional mixing, granulating, dragee-making, dissolving, lyophilizing processes. The processes to be used will depend ultimately on the physical properties of the active ingredient used.

Suitable excipients are, in particular, fillers such as sugars for example, lactose, sucrose, mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Oral dosage forms may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, including for example, sodium carboxymethyl cellulose, sorbitol and/or dextran. Such compositions may also comprise adjuvants such as preserving, wetting, emulsifying, and dispensing agents. They may also be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

In addition to administration with conventional carriers, active ingredients may be administered by a variety of specialized delivery drug techniques which are known to those of skill in the art, such as portable infusion pumps.

The pussy-toe compositions of the present invention are administered along with a pharmaceutically acceptable carrier in an amount sufficient to prevent inflammation and pruritis and/or treat existing disorders involving inflammation and/or pruritis. Pussy-toes extract has extremely low toxicity and a low degree of side effects even at high doses. The dosing range of the pussy-toes extract will vary depending on a number of factors, such as whether it is used for prophylaxis or treatment of an active disorder, route of administration, dosing schedule, etc. In general, the therapeutic dose of pussy-toes plant extract may range between about 0.1–1000 mg/kg/day, with between about 1–100 mg/kg/day being preferred. The foregoing doses may be administered as a single dose or may be divided into multiple doses for administration. The pussy-toes compositions may be administered once to several times daily. For preventative purposes, a typical dosing schedule could be, for example, 0.1–1000 mg/kg weekly beginning 1–2 weeks prior to exposure to an allergen, virus, irritant, or other agent capable of causing an inflammatory/pruritic response, taken up until 1–2 weeks post-exposure.

Other drugs besides pussy-toes plant extract which are compatible with the carrier ingredients may also be incorporated into the carrier. Such drugs may be readily ascertained by those of ordinary skill in the art and may include, for instance, antibiotics, antivirals, corticosteroids, antihistamines, drying agents, antiinflammatory agents, etc. Similarly, other compatible inactive ingredients including, but not limited to, fillers, binders, lubricants, fragrances, preservatives, dyes, etc. may be included in the carrier. If included, such ingredients will typically comprise from about 0.001–10% by weight of the composition. Such ingredients may be readily ascertained by persons skilled in the art.

In one embodiment of the invention, the pussy-toes compounds are used to prevent and treat inflammatory/pruritic lesions caused by one or more of the following disorders: poison ivy, chicken pox, or cold sores. In this regard, it has been surprisingly found that when ingested or otherwise administered prior to exposure to the trigger (i.e. plant, virus, etc.) that causes the disorder, pussy-toes extract is effective in preventing a rash, lesion, or other inflammatory response and/or pruritis that normally results from exposure to said trigger. Further, pussy-toes is effective in treating an existing rash, lesion, or other inflammatory response and/or pruritis in a patient by administration of pussy-toes extract orally, topically, or otherwise one or more times per day. Following administration of pussy-toes extract, the itching or other discomfort associated with the rash or lesion lessens or ceases altogether, and the rash or lesion dries up and dissipates.

EXAMPLE 1

Preparation of Pussy-Toes Extract

Leaves from pussy-toes plant are placed in 3–4 ounces of distilled water that has been preheated to near boiling. The leaves are allowed to steep in the water for a few seconds to a minute, and are then removed. The aqueous extract formed may then be stored by refrigeration until ready to use, or used immediately.

EXAMPLE 2

Treatment of Poison Ivy, Chicken Pox, and Cold Sores

Aqueous extract as described in Example 1 was administered to fifteen patients having lesions from poison ivy, chicken pox, or cold sores, by saturating a cotton ball with the aqueous extract, then applying the extract to the lesions four times daily. Within 24–36 hours, the lesions on the patients had dried up, the inflammation and pruritis reduced, and the lesions disappeared at an accelerated rate.

It should be appreciated that minor dosage and formulation modifications of the composition and the ranges expressed herein may be made and still come within the scope and spirit of the present invention. Having described the invention with reference to particuiar compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A composition for treatment of inflammation and/or pruritis comprising an effective amount of an aqueous extract from the leaves of field pussy-toes; and a pharmaceutically acceptable carrier.

2. The composition of claim 1 wherein the carrier is selected from the group consisting of a gel capsule, distilled water, tablet, pill, powder, granule, microcapsule, nutritional supplement, food additive, drops, liquid, solution, suspension, beverage, rinse, mouthwash, gargle, pill, capsule, lozenge, cough drop, towellette, transdermal patch, ointment, salve, cream, lotion, gel, inhaler, emulsion, suppository, syrup, and a paste.

3. The composition of claim 1, comprising between about 0.001–1000 mg of the field pussy-toes leaf extract.

4. The composition of claim 1 further comprising an inactive ingredient selected from the group consisting of a filler, lubricant, binder, fragrance, dye, and a preservative.

* * * * *